United States Patent
Ragheb

(10) Patent No.: US 10,159,597 B2
(45) Date of Patent: Dec. 25, 2018

(54) BIRTH CONTROL ASSEMBLY

(71) Applicant: Gamal Ragheb, Marblehead, MA (US)

(72) Inventor: Gamal Ragheb, Marblehead, MA (US)

( * ) Notice: Subject to any disclaimer, the term of this patent is extended or adjusted under 35 U.S.C. 154(b) by 326 days.

(21) Appl. No.: 15/137,544

(22) Filed: Apr. 25, 2016

(65) Prior Publication Data

US 2017/0304109 A1 Oct. 26, 2017

(51) Int. Cl.
*A61F 6/14* (2006.01)

(52) U.S. Cl.
CPC .................... *A61F 6/146* (2013.01)

(58) Field of Classification Search
CPC .......... A61F 6/146; A61F 6/225; A61F 6/065; A61F 6/18; A61F 6/04; A61F 2006/047; A61F 6/00; A61B 2017/1205
See application file for complete search history.

(56) References Cited

U.S. PATENT DOCUMENTS

| | | | |
|---|---|---|---|
| 3,704,704 A * | 12/1972 | Gonzales | A61F 6/24 128/831 |
| 5,353,811 A | 10/1994 | Davis et al. | |
| 5,769,090 A | 6/1998 | Brown | |
| 6,223,747 B1 * | 5/2001 | Rudge | A61F 6/065 128/844 |
| D620,592 S | 7/2010 | VanDenBogart et al. | |
| 8,728,140 B2 | 5/2014 | Feemster et al. | |
| 2004/0250334 A1 * | 12/2004 | El-Raghy | A41D 19/0055 2/159 |
| 2013/0296643 A1 | 11/2013 | Hoyte et al. | |

FOREIGN PATENT DOCUMENTS

WO WO8601998 4/1986

* cited by examiner

*Primary Examiner* — Ophelia A Hawthorne

(57) ABSTRACT

A birth control assembly for inhibiting sperm from entering a uterus includes a tube that may be inserted into a cervix. A valve is coupled to the tube. The valve inhibits sperm from entering the tube thereby facilitating the tube to control birth. The valve facilitates menstrual fluid to exit the cervix.

4 Claims, 3 Drawing Sheets

BIRTH CONTROL ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to birth control devices and more particularly pertains to a new birth control device for inhibiting sperm from entering a uterus and facilitating menstrual fluid to exit the uterus.

BRIEF SUMMARY OF THE INVENTION

An embodiment of the disclosure meets the needs presented above by generally comprising a tube that may be inserted into a cervix. A valve is coupled to the tube. The valve inhibits sperm from entering the tube thereby facilitating the tube to control birth. The valve facilitates menstrual fluid to exit the cervix.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
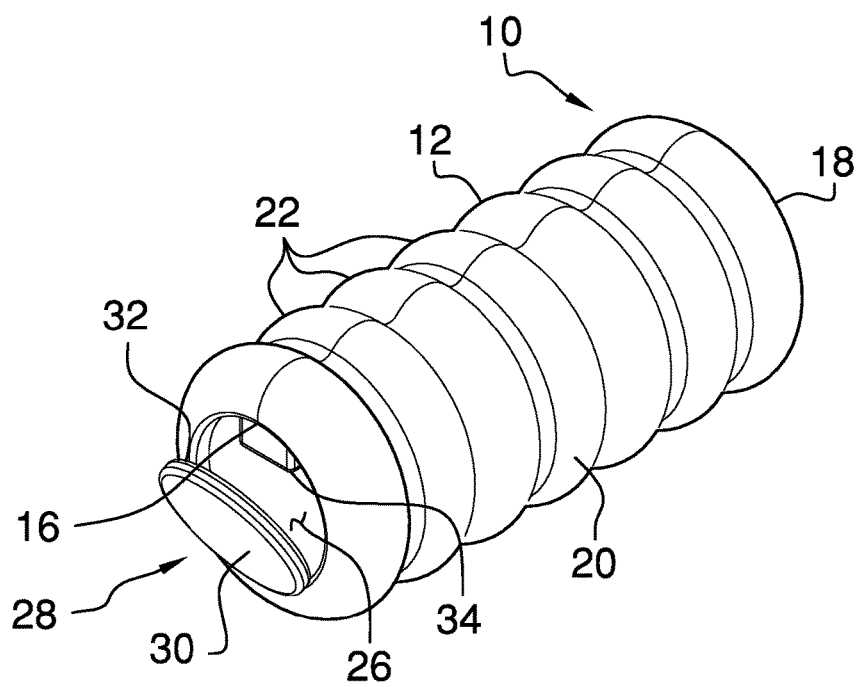
FIG. 1 is a perspective view of a birth control assembly according to an embodiment of the disclosure.
Figure 2:
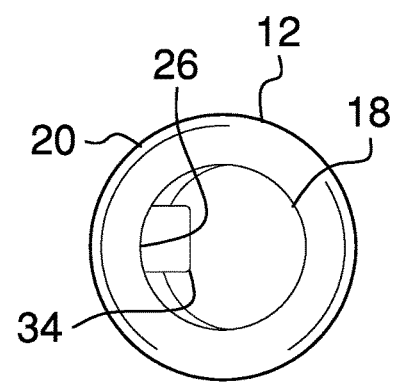
FIG. 2 is a top view of an embodiment of the disclosure.
Figure 3:
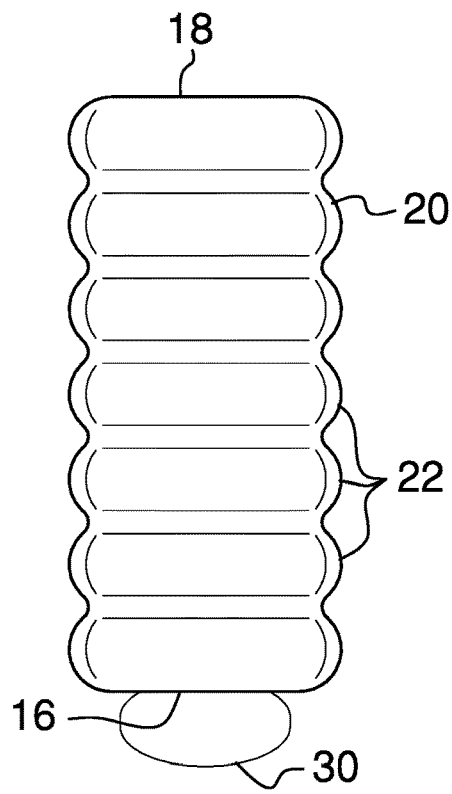
FIG. 3 is a back view of an embodiment of the disclosure.
Figure 4:
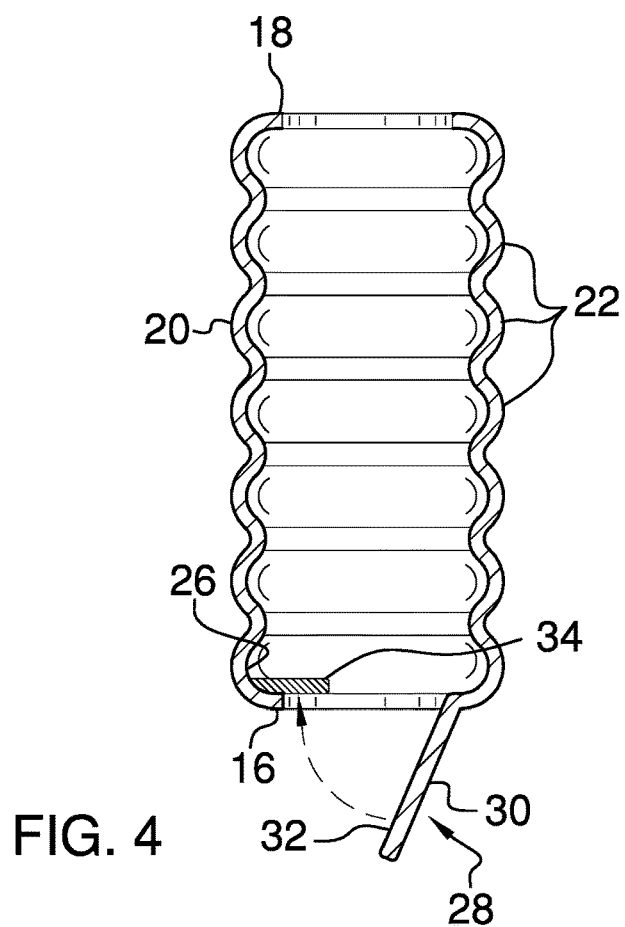
FIG. 4 is a cross sectional view taken along line 4-4 of FIG. 1 of an embodiment of the disclosure.
Figure 5:
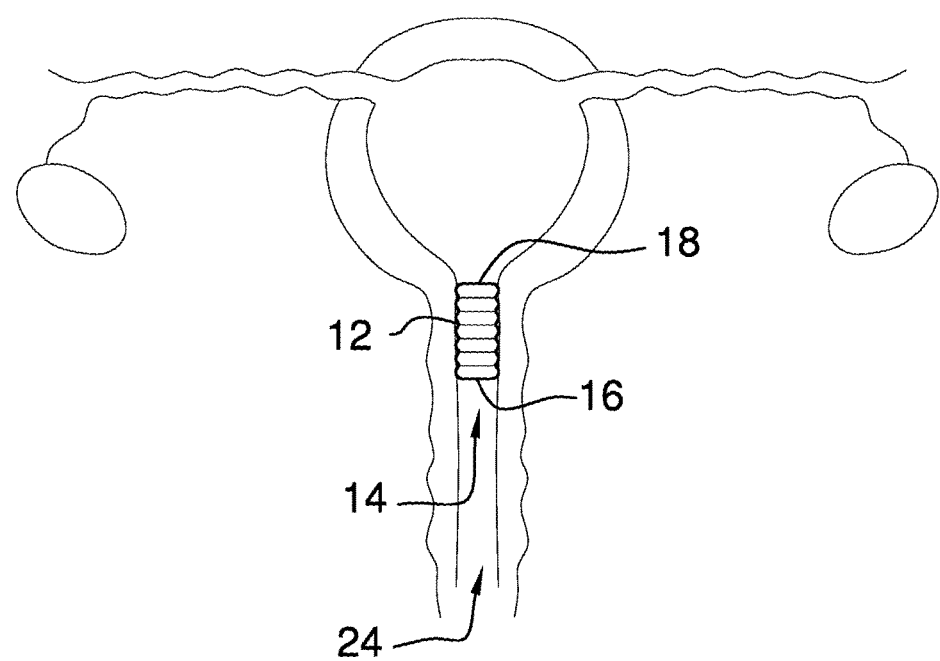
FIG. 5 is a perspective in-use view of an embodiment of the disclosure.

With reference now to the drawings, and in particular to FIGS. 1 through 5 thereof, a new birth control device embodying the principles and concepts of an embodiment of the disclosure and generally designated by the reference numeral 10 will be described.

As best illustrated in FIGS. 1 through 5, the birth control assembly 10 generally comprises a tube 12 that may be inserted into a cervix 14. The tube 12 has a first end 16, a second end 18 and an outer wall 20 extending therebetween. The outer wall 20 comprises a plurality of rings 22 that are distributed between the first end 16 and the second end 18. Each of the rings 22 may frictionally engage the cervix 14. Thus, the tube 12 is retained in the cervix 14 having the first end 16 being directed toward an opening 24 of the cervix 14. The outer wall 20 has an inner surface 26. Moreover, the tube 12 is comprised of a hypo-allergenic metal such as titanium or the like.

A valve 28 is coupled to the tube 12. The valve 28 inhibits sperm from entering the tube 12 thereby facilitating the tube 12 to control birth. The valve 28 allows menstrual fluid to exit the cervix 14. Thus, the valve 28 facilitates fluid to exit the first end 16 of the tube 12 and the valve 28 restricts fluid from entering the first end 16 of the tube 12.

The valve 28 comprises a door 30 that is hingedly coupled to the tube 12. The door 30 is positioned on the first end 16 and the door 30 selectively opens and closes the first end 16. The door 30 has a first surface 32 and the door 30 swings outwardly from the tube 12 when the door 30 is in the open position. The first surface 32 abuts the first end 16 when the door 30 is in the closed position. Thus, the first surface 32 forms a fluid impermeable seal with the tube 12. The door 30 is comprised of a magnetic material.

A retainer 34 is provided and the retainer 34 is coupled to the tube 12. The retainer 34 is positioned on the inner surface 26 of the tube 12. The retainer 34 is aligned with the first end 16 of the tube 12. The retainer 34 may comprise a magnet or the like.

The retainer 34 biases the door 30 into the closed position. Thus, the door 30 may inhibit the sperm from entering the tube 12. The retainer 34 releases the door 30 into the open position when the menstrual fluids enter the second end 18 of the tube 12. The menstrual fluids urge the door 30 into the open position. Thus, the door 30 facilitates the menstrual fluids to flow outwardly from the cervix 14.

In use, the tube 12 is inserted into the cervix 14 having the first end 16 of the tube 12 facing the opening 26 of the cervix 16. The retainer 34 urges the door 30 into the closed position. Thus, the sperm is inhibited from entering the tube 12. The menstrual fluids enter the second end 18 of the tube 12 when the user menstruates. The menstrual fluid urges the door 30 into the open position. Thus, the menstrual fluid may flow outwardly from the tube 12.

The tube 12 remains in the cervix 14 for a selected duration of time. The tube 12 is removed from the cervix 14 at any selected time. Moreover, the tube 12 may be removed and re-inserted into the cervix 14 multiple times. The tube 12 may be cleaned and sterilized when the tube 12 is removed from the cervix 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A birth control assembly configured to inhibit sperm from entering a uterus, said assembly comprising:
   a tube being configured to be inserted into a cervix, said tube having a first end, a second end and an outer wall extending therebetween, said outer wall comprising a plurality of rings being distributed between said first end and said second end, each of said rings being configured to frictionally engage the cervix thereby facilitating said tube to be retained in the cervix having said first end being directed toward an opening of the cervix, said outer wall having an inner surface; and
   a valve being coupled to said tube, said valve being configured to inhibit sperm from entering said tube thereby facilitating said tube to control birth, said valve being configured to facilitate menstrual fluid to exit the cervix, said valve comprising a door being hingedly coupled to said tube, said door being positioned on said first end such that said door selectively opens and closes said front end, said door having a first surface, said door swinging outwardly from said tube when said door is in said open position, said first surface abutting said first end when said door is in said closed position such that said first surface forms a fluid impermeable seal with said tube.

2. The assembly according to claim 1, wherein said tube is comprised of a hypo-allergenic metal.

3. The assembly according to claim 1, further comprising a retainer being coupled to said tube, said retainer being positioned on said inner surface of said tube, said retainer being aligned with said first end, said retainer biasing said door into said closed position wherein said door is configured to inhibit the sperm from entering said tube, said retainer releasing said door into said open position when the menstrual fluids enter said second end of said tube wherein said door is configured to facilitate the menstrual fluids to flow outwardly from the cervix.

4. A birth control assembly configured to inhibit sperm from entering a uterus, said assembly comprising:
   a tube being configured to be inserted into a cervix, said tube having a first end, a second end and an outer wall extending therebetween, said outer wall comprising a plurality of rings being distributed between said first end and said second end, each of said rings being configured to frictionally engage the cervix thereby facilitating said tube to be retained in the cervix having said first end being directed toward an opening of the cervix, said outer wall having an inner surface, said tube being comprised of a hypo-allergenic metal; and
   a valve being coupled to said tube, said valve being configured to inhibit sperm from entering said tube thereby facilitating said tube to control birth, said valve being configured to facilitate menstrual fluid to exit the cervix, said valve comprising:
      a door being hingedly coupled to said tube, said door being positioned on said first end such that said door selectively opens and closes said front end, said door having a first surface, said door swinging outwardly from said tube when said door is in said open position, said first surface abutting said first end when said door is in said closed position such that said first surface forms a fluid impermeable seal with said tube, and
      a retainer being coupled to said tube, said retainer being positioned on said inner surface of said tube, said retainer being aligned with said first end, said retainer biasing said door into said closed position wherein said door is configured to inhibit the sperm from entering said tube, said retainer releasing said door into said open position when the menstrual fluids enter said second end of said tube wherein said door is configured to facilitate the menstrual fluids to flow outwardly from the cervix.

* * * * *